(12) United States Patent
Anderson et al.

(10) Patent No.: US 10,190,894 B2
(45) Date of Patent: Jan. 29, 2019

(54) TECHNOLOGIES FOR CONTROLLING DEGRADATION OF SENSING CIRCUITS

(71) Applicant: Intel Corporation, Santa Clara, CA (US)

(72) Inventors: Glen J. Anderson, Beaverton, OR (US); John C. Weast, Portland, OR (US); Tobias M. Kohlenberg, Portland, OR (US); Brian D. Johnson, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 179 days.

(21) Appl. No.: 14/998,309

(22) Filed: Dec. 26, 2015

(65) Prior Publication Data

US 2017/0184563 A1    Jun. 29, 2017

(51) Int. Cl.
*G01D 11/24* (2006.01)
*G01N 33/24* (2006.01)
*H04Q 9/00* (2006.01)
*G01N 33/18* (2006.01)

(52) U.S. Cl.
CPC ....... *G01D 11/245* (2013.01); *G01N 33/1886* (2013.01); *G01N 33/24* (2013.01); *H04Q 9/00* (2013.01); *H04Q 2209/43* (2013.01); *H04Q 2209/86* (2013.01)

(58) Field of Classification Search
CPC .. H04Q 2209/86; H04Q 2209/43; H04Q 9/00; G01D 11/245; G01N 33/24
See application file for complete search history.

(56) References Cited

U.S. PATENT DOCUMENTS

| | | | | |
|---|---|---|---|---|
| 5,177,660 A * | 1/1993 | Kilner | ............ | B65D 33/00 |
| | | | | 361/212 |
| 5,279,607 A * | 1/1994 | Schentag | ............ | A61B 5/0031 |
| | | | | 604/114 |
| 5,401,778 A * | 3/1995 | Tokiwa | ............ | C08L 67/04 |
| | | | | 523/124 |
| 6,791,029 B2 * | 9/2004 | Mori | ............ | H05K 5/00 |
| | | | | 174/520 |

(Continued)

FOREIGN PATENT DOCUMENTS

| | | | | |
|---|---|---|---|---|
| JP | 2006-242933 | | 9/2006 | |
| JP | WO 2007034905 A1 * | | 3/2007 | ............ C08L 33/08 |

OTHER PUBLICATIONS

Hwang, Suk-Won, et al. "High-Performance Biodegradable/Transient Electronics on Biodegradable Polymers." Advanced Materials 26.23 (2014): 3905-3911.*

(Continued)

*Primary Examiner* — Harshad R Patel
*Assistant Examiner* — Punam P Roy
(74) *Attorney, Agent, or Firm* — Barnes & Thornburg LLP

(57) ABSTRACT

Technologies for controlling degradation of a sensor mote including detecting a trigger event and initiating degradation of at least a portion of the sensor mote in response to the trigger event. The trigger event may be embodied as any type of event detectable by the sensor mote such as a trigger signal, particular sensed data, expiration of a reference time period, completion of a task, and so forth. The sensor mote may imitate the degradation by, for example, controlling a valve to release a chemical stored in the sensor mote or allow a substance into the sensor mote.

22 Claims, 6 Drawing Sheets

(56) References Cited

U.S. PATENT DOCUMENTS

| | | | | |
|---|---|---|---|---|
| 6,929,636 | B1* | 8/2005 | von Alten | A61B 5/073 604/890.1 |
| 6,975,245 | B1 | 12/2005 | Slater et al. | |
| 7,318,010 | B2* | 1/2008 | Anderson | H04W 52/0219 340/521 |
| 8,063,774 | B2* | 11/2011 | Anderson | G01D 11/245 340/539.26 |
| 8,262,960 | B2* | 9/2012 | Kimura | B27N 3/02 264/120 |
| 9,251,698 | B2* | 2/2016 | Vian | G08C 17/02 |
| 9,294,098 | B2* | 3/2016 | Shah | H03K 19/17768 |
| 9,650,489 | B2* | 5/2017 | Katayama | B09B 3/00 |
| 9,760,691 | B2* | 9/2017 | Seeger | A61J 7/0418 |
| 2003/0139661 | A1 | 7/2003 | Kimchy et al. | |
| 2006/0080819 | A1* | 4/2006 | McAllister | G06K 17/00 29/403.3 |
| 2007/0039745 | A1* | 2/2007 | Anderson | A01B 79/005 172/6 |
| 2008/0140185 | A1* | 6/2008 | Kiser | C08G 18/10 623/1.42 |
| 2008/0219122 | A1* | 9/2008 | Detzler | G06F 21/554 369/83 |
| 2009/0018235 | A1* | 1/2009 | Nascimento | C08L 67/04 523/128 |
| 2009/0303071 | A1 | 12/2009 | Anderson | |
| 2010/0081895 | A1 | 4/2010 | Zand | |
| 2010/0247278 | A1* | 9/2010 | Beck | F41F 5/00 414/467 |
| 2011/0276124 | A1* | 11/2011 | Doerr | A61F 2/82 623/1.15 |
| 2012/0223293 | A1* | 9/2012 | Borenstein | B82Y 10/00 257/40 |
| 2013/0140649 | A1* | 6/2013 | Rogers | H01L 29/66 257/414 |
| 2014/0305900 | A1* | 10/2014 | Rogers | H05K 13/0023 216/13 |
| 2016/0144030 | A1* | 5/2016 | Floyd, III | A61N 5/06 424/452 |
| 2016/0378981 | A1* | 12/2016 | Cutler | F24F 5/0046 726/23 |
| 2017/0045487 | A1* | 2/2017 | Bauer-Reich | G01N 33/24 |
| 2017/0189553 | A1* | 7/2017 | Hunter | A61K 49/00 |

OTHER PUBLICATIONS

Hernandez, Hector Lopez, et al. "Triggered transience of metastable poly (phthalaldehyde) for transient electronics." Advanced Materials 26.45 (2014): 7637-7642.*

N. Banerjee, Y. Xie, H. Kim and C. H. Mastrangelo, "Microfluidic device for triggered chip transience," 2013 IEEE Sensors, Baltimore, MD, 2013, pp. 1-4.*

Huang, Xian, et al. "Biodegradable materials for multilayer transient printed circuit boards." Advanced Materials 26.43 (2014): 7371-7377.*

Fu, Kun, et al. "Transient rechargeable batteries triggered by cascade reactions." Nano letters 15.7 (2015): 4664-4671.*

Hwang, Suk-Won, et al. "Materials and Fabrication Processes for Transient and Bioresorbable High-Performance Electronics." Advanced Functional Materials 23.33 (2013): 4087-4093.*

Park, Chan Woo, et al. "Thermally triggered degradation of transient electronic devices." Advanced Materials 27.25 (2015): 3783-3788.*

Hwang, Suk-Won, et al. "A physically transient form of silicon electronics." Science 337.6102 (2012): 1640-1644.*

Hoare, Todd, et al. "A magnetically triggered composite membrane for on-demand drug delivery." Nano letters 9.10 (2009): 3651-3657.*

S. S. Pandey and C. H. Mastrangelo, "An exothermal energy release layer for microchip transience," 2013 IEEE Sensors, Baltimore, MD, 2013, pp. 1-4.*

Lee, Chi Hwan, et al. "Materials and wireless microfluidic systems for electronics capable of chemical dissolution on demand." Advanced Functional Materials 25.9 (2015): 1338-1343.*

Sim, Kyoseung, et al. "Destructive electronics from electrochemical-mechanically triggered chemical dissolution." Journal of Micromechanics and Microengineering 27.6 (2017).*

M. Luo, A. W. Martinez, C. Song, F. Herrault and M. G. Allen, "A Microfabricated Wireless RF Pressure Sensor Made Completely of Biodegradable Materials," in Journal of Microelectromechanical Systems, vol. 23, No. 1, pp. 4-13, Feb. 2014.*

"Biodegradable." Academic Press Dictionary of Science and Technology, edited by Christopher G. Morris, Elsevier Science & Technology, 4th edition, 1992. Credo Reference, https://search.credoreference.com/content/entry/apdst/biodegradable/0?institutionId=743. Accessed Mar. 16, 2018.*

Albertsson, Ann-Christine, and Sigbritt Karlsson. "Aspects of biodeterioration of inert and degradable polymers." International biodeterioration & biodegradation 31.3 (1993): 161-170.*

Costache, M. C., et al. "Tyrosine-derived polycarbonate-silica xerogel nanocomposites for controlled drug delivery." Acta biomaterialia 9.5 (2013): 6544-6552.*

International Search Report for PCT application No. PCT/US2016/063578, dated Mar. 8, 2017 (6 pages).

Written Opinion for PCT application No. PCT/US2016/063578, dated Mar. 8, 2017 (7 pages).

* cited by examiner

US 10,190,894 B2

TECHNOLOGIES FOR CONTROLLING DEGRADATION OF SENSING CIRCUITS

BACKGROUND

Sensing systems incorporating large number of sensors are being developed for various applications. For example, some Internet of Things (IoT) applications may include hundreds or thousands of sensors. In many cases, the individual sensors may be designed as self-contained sensing platforms configured to report sensor data periodically or in response to an interrogation signal (e.g., in the case of radio frequency identification (RFID) applications). The array of sensors is often deployed across or in an area of interest to acquire various sensor data indicative of stimulus of interest. For example, in farming applications, an array of sensors may be implanted into the ground to sense various aspects of the soil. However, the use of a large number of sensors in the soil can lead to soil contamination by the sensors if not removed. Unfortunately, the recovery of the sensors from the soil can be tedious and error prone.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements.

DETAILED DESCRIPTION OF THE DRAWINGS

Figure 1:
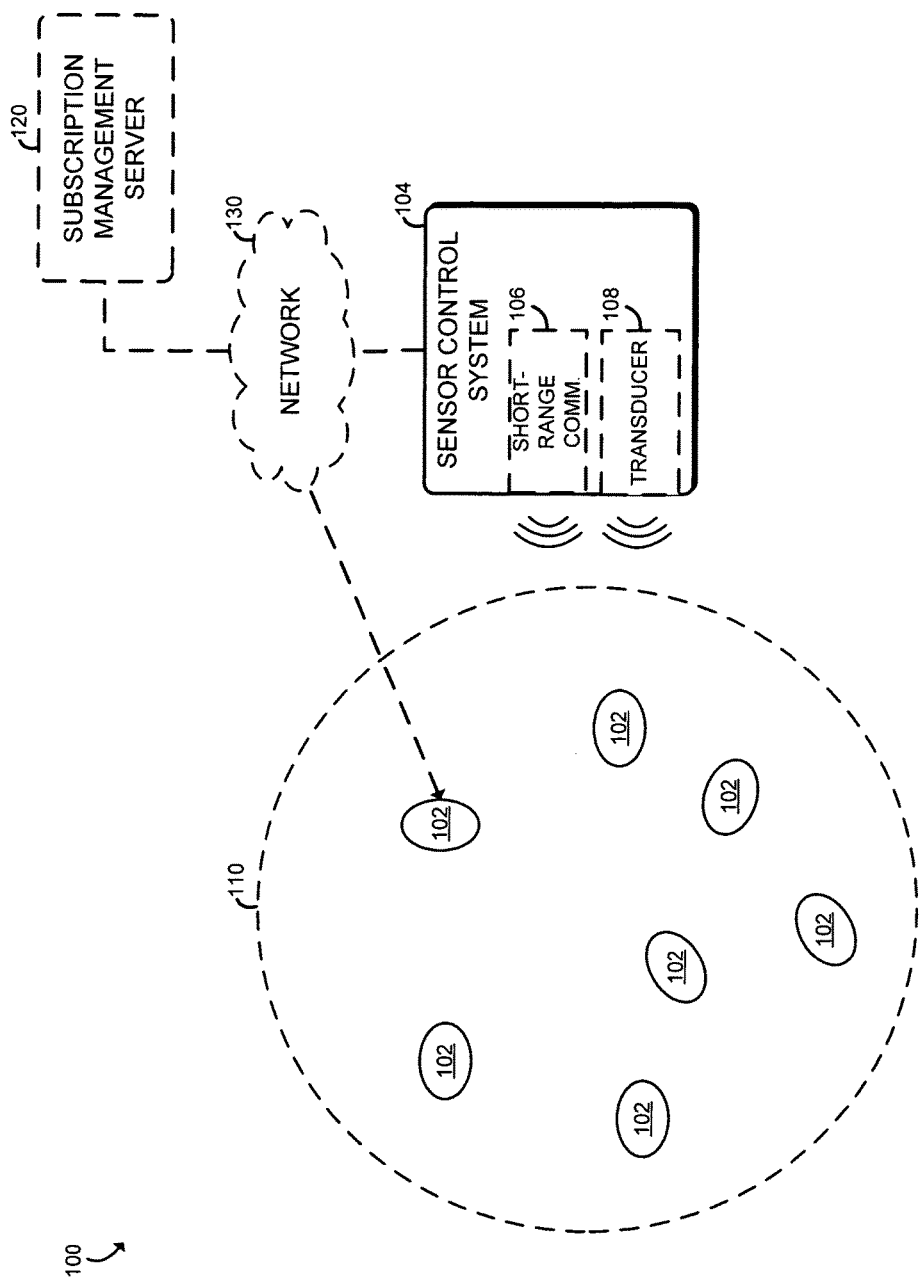
FIG. 1 is a simplified block diagram of at least one embodiment of a system for controlling degradation of sensor motes.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, in an illustrative embodiment, a system 100 for controlling degradation of sensor motes includes one or more sensor motes 102 and a sensor control system 104. As discussed in more detail below, the sensor motes 102 are embodied as self-contained sensing devices configured to produce sensor data indicative of a stimulus, such as a change in or a characteristic of an environment in which the sensor motes 102 are deployed. The particular stimuli the sensor motes 102 are configured to sense or monitor may vary depending on the particular application or implementation. Illustratively, the sensor motes 102 are distributed about a sensing location 110. For example, the sensor motes 102 may be implanted in a section of soil to monitor and/or manage various characteristics of the soil. As part of the sensing function of the sensor motes 102, each sensor mote 102 may be configured to transmit any produced sensor data to the sensor control system 104 periodically or in response to an interrogation signal. For example, in the illustrative embodiment, the sensor motes 102 may transmit sensor data in response to receiving an interrogation signal from the sensor control system 104. The interrogation signal may be embodied as, for example, a radio-frequency identification (RFID) signal, a magnetic field signal, a sonic signal, and/or other type of signal capable of prompting the sensor mote 102 to relay its sensed data to the sensor control system 104.

In addition to the sensing functions performed by the sensor motes 102, each sensor mote 102 is configured to self-degrade in response to detection of a trigger event. As discussed in more detail below, at least a portion of each sensor mote 102 is biodegradable, and each sensor mote is configured to initiate the degradation of that portion in response to detecting a trigger event. The trigger event may be embodied as any type of event detectable by the sensor motes 102 including, but not limited to, a trigger signal such as a wireless communication signal, the sensor data satisfying a reference threshold or change, expiration of a timer, completion of a predefined function of the sensor mote 102, a security event, and/or other event discernable by the sensor motes 102. To support the degradation of the portion of the sensor mote 102, each sensor mote 102 may include a chemical payload in some embodiments. In such embodiments, the sensor motes 102 are configured to control release of a chemical from the chemical payload to initiate degradation of components of the sensor mote 102. In other embodiments, the sensor mote 102 may be configured to control the intake of substances external to the sensor mote 102 to cause the degradation of components internal to the sensor mote 102. For example, the external substances may react with a chemical payload held within the sensor mote 102. Additionally, to increase the degradation effect on the array of sensor motes 102, one or more sensor motes 102 may be configured to propagate the trigger event by transmitting trigger signals to other sensor motes 102, releasing chemicals to initiate degradation of the other sensor motes 102, and/or the like. In this way, each sensor mote 102 is configured to degrade in response to a trigger event. As such, unlike typical sensing circuits or devices which must be recovered from the sensing location 110 (e.g., dug up from the soil), the sensor motes 102 are configured to degrade such that no recovery of critical components of the sensor motes 102 is required.

As discussed above, the sensor control system 104 may be configured to communicate with the sensor motes 102 to receive sensor data from the sensor motes 102 and/or to initiate the degradation of the sensor motes 102 (e.g., by transmitting at trigger signal as discussed below). As such, the sensor control system 104 may be embodied as any type of compute device capable of communicating with the sensor motes 102. For example, the sensor control system 104 may be embodied as or otherwise include, without limitation, a computer, a smartphone, a tablet computer, a notebook computer, a laptop computer, a mobile compute device, a server, a server system, an analysis compute device, a networking device, a multiprocessor system, a processor-based system, a consumer electronic device, a desktop computer, a wearable computer, a smart accessory such as a smart watch or smart glasses, a messaging device, and/or any other computing device capable of communicating with the sensor motes 102. As such, the sensor control system 104 may include components commonly found in a compute device such as a processor, memory, I/O subsystem, data storage, communication subsystem, etc. The description of those common components is not included herein for clarity of the description.

In the illustrative embodiment, the sensor control system 104 may also include a short-range communication circuit 106 and/or a transducer 108. The short-range communication circuit 106 may be embodied as any type of communication circuit or device capable of communicating with the sensor motes 102 within a relatively short range. For example, in the illustrative embodiment, the short-range communication circuit 106 is embodied as an RFID communication circuit configured to communicate with the sensor motes 102 by providing an interrogation signal usable by the sensor motes 102 to power components thereof. However, in other embodiments, the short-range communication circuit 106 may be embodied as other types of electromagnetic interrogation circuits. Of course, in other embodiments, the short-range communication circuit 106 may be embodied as wireless communication circuit configured to communicate with the sensor motes 102 utilizing a short-ranged communication protocol such as a Bluetooth communication protocol.

The transducer 108 may be configured as any type of device or circuit capable of generating a sonic wave and transmitting the sonic wave to the sensing location 110. For example, in some embodiments as discussed below, each sensor mote 102 may include a number of predefined breakable fissures, which may be broken by the application of a sonic wave from the transducer 108. The breaking of the fissures of the sensor motes 102 may initiate the degradation of the sensor motes 102 as discussed in detail below.

Although the illustrative system 100 of FIG. 1 includes a single sensor control system 104, it should be appreciated that the system 100 may include additional sensor control systems 104 in other embodiments. For example, in some embodiments, multiple sensor controls systems 104 may be place about (e.g., around the perimeter) of the sensing location 110 to facilitate communication with each sensor mote 102. In such embodiments, the sensor control systems 104 may be configured to communicate with each other to facilitate communication and control of the sensor motes 102 (e.g., to control the degradation of the sensor motes 102 as discussed herein).

In some embodiments, the system 100 may also include a subscription management server 120, which may communicate with the sensor control system(s) 104 and/or directly with the sensor motes 102 via a network 130. In the illustrative embodiment, the subscription management server 120 is configured to manage a subscription service related to the use of the sensor motes 102. In such embodiments, the subscription management server 120 controls the initiation of the degradation of the sensor motes 102. For example, if the subscription management server 120 determines that a subscription service associated with the sensor motes 102 has expired, the subscription management server 120 may transmit a trigger signal to the sensor control system 104, which is configured to relay the trigger signal to the sensor motes 102, to cause the initiation of the degradation of the sensor motes 102. In other embodiments, the subscription management server 120 may communicate the trigger signal directly with the sensor motes 102.

The subscription management server 120 may be embodied as any type of server computer capable of managing a subscription service related to the use of the sensor motes 102. For example, the subscription management server 120 may be embodied as, without limitation, a server computer, a distributed computing system, a networking device, a multiprocessor system, a consumer electronic device, a smart appliance, and/or any other computing device capable of performing the functions described herein. As such, the subscription management server 120 may include components commonly found in a server computer, such as a processor, memory, I/O subsystem, data storage, communication subsystem, etc. The description of those common components is not included herein for clarity of the description.

As discussed above, the subscription management server 120 may communicate with the sensor control system 104 and/or the sensor motes 102 via the network 130. The network 130 may be embodied as any number of various wired and/or wireless networks. For example, the network 130 may be embodied as, or otherwise include, a wired or wireless local area network (LAN), a wired or wireless wide area network (WAN), a cellular network, and/or a publicly-accessible, global network such as the Internet. As such, the network 130 may include any number of additional devices, such as additional computers, routers, and switches, to facilitate communications among the devices of the system 100.

As discussed above, the sensor motes 102 are embodied as self-contained sensing devices or circuits configured for deployment in the sensing location 110, which may be embodied as soil, water, or other environmental location. For example, in the illustrative embodiment, each sensor mote 102 is designed to have a relatively small footprint such that the sensor mote 102 can be integrated into the sensing location 110 without adversely affecting the natural functions occurring in the sensing location 110. Several illustrative embodiments of the sensor motes 102 are shown in FIGS. 2-5 with the understanding that the other configurations of the sensor motes 102 are possible, which may combine aspects of the various embodiments of FIGS. 2-5, for example.

Figure 2:
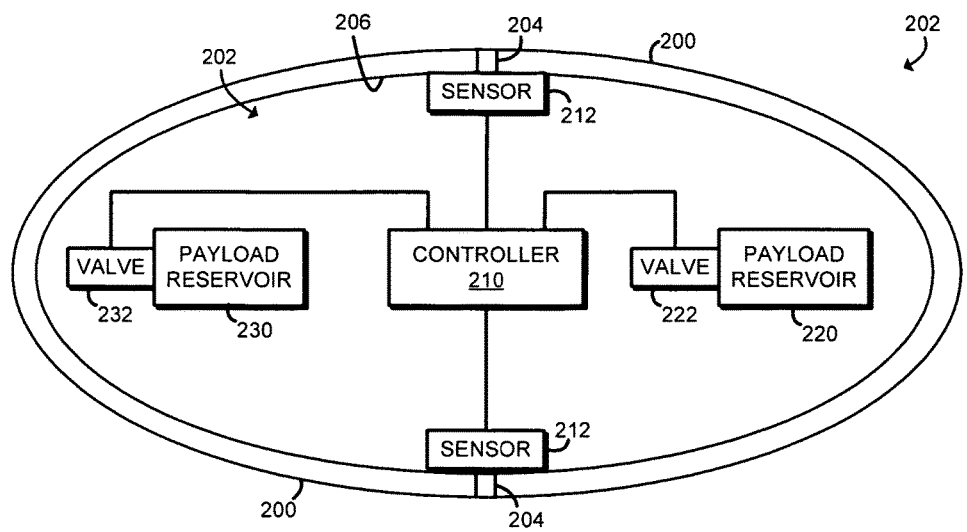
FIG. 2 is a simplified block diagram of at least one embodiment of a sensor mote of the system of FIG. 1.

In the illustrative embodiment of FIG. 2, each sensor mote 102 includes a housing or shell 200 that defines an inner chamber 202. The housing 200 may have any suitable shape conducive to the deployment of the sensor mote 102 into the sensing location 110. In the illustrative embodiment, the sensor motes 102 have a substantial oval shape, but may have other shapes in other embodiments. Additionally, in the illustrative embodiment, the housing 200 or a portion thereof is made from a biodegradable material.

Each sensor mote 102 includes various components, including a controller 210 and one or more sensors 212, located within the inner chamber 202 of the housing 200. As discussed in more detail below in regard to FIG. 6, the controller 210 may be embodied as any type of microcontroller or processor capable of controlling the functionality of the sensor mote 102. In the illustrative embodiment, the controller 210 is embodied as an integrated circuit, such as a System-on-a-Chip (SoC) device, sized to be positioned within the inner chamber 202. Additionally, in some embodiments, at least a portion of the controller 210 may be biodegradable, in addition to or alternatively to the housing 200.

In use, the controller 210 controls the acquisition of sensor data from the sensors 212. Each of the sensors 212 may be embodied as any type of sensor capable of producing sensor data indicative of a stimulus. To facilitate the sensing of stimuli external to the sensor mote 102, the sensors 212 may be exposed to the environment external to the inner chamber 202 via a corresponding sensor passageway 204 defined through the housing 200. In such embodiments, sensor 212 may be coupled to an inner wall 206 of the housing 200 so as to create a seal around the sensor passageway 204 as shown in FIG. 2. The sensor data produced by each sensor 212 is provided to the controller 210.

As discussed above, each sensor mote 102 is configured to initiate degradation of at least a portion of the sensor mote 102 in response to a trigger event. In some embodiments, as discussed in more detail below, the controller 210 may be configured to control the initiation of the degradation. Additionally, to support the degradation of the sensor mote 102, each sensor mote 102 may include one or more chemical payloads, which may store a chemical to be released to initiate or accelerate the degradation of the sensor mote 102.

For example, in the illustrative embodiment of FIG. 2, the sensor mote 102 includes a payload reservoir 220, which is configured to store a chemical capable of degrading or accelerating the degradation of the controller 210. For example, the chemical stored in the payload reservoir 220 may be embodied as chemical capable of initiating or accelerating the degradation of a biodegradable portion of the controller 210. As discussed above, the controller 210 is configured to control initiation of the degradation of the sensor mote 102. To do so, in the illustrative embodiment of FIG. 2, the controller 210 controls operation of a valve 222 of the payload reservoir 220 to control the release of the chemical stored therein. In some embodiments, as shown in FIG. 2, the payload reservoir 220 may be positioned within the inner chamber 202 such that the valve 222 faces the controller 210 to improve the contact of the released chemical with the controller 210.

In some embodiments, the sensor mote 102 may additionally or alternatively include a payload reservoir 230 configured to store a chemical capable of degrading or accelerating the degradation of the housing 200. For example, the chemical stored in the payload reservoir 230 may be embodied as chemical capable of initiating or accelerating the degradation of a biodegradable portion of the housing 200. Again, the controller 210 is configured to control a valve 232 of the payload reservoir 230 to control the release of the chemical stored therein. In some embodiments, as shown in FIG. 2, the payload reservoir 220 may be positioned within the inner chamber 202 such that the valve 232 faces the inner wall 206 of the housing 200 to improve the contact of the released chemical with the housing 200.

Figure 3:
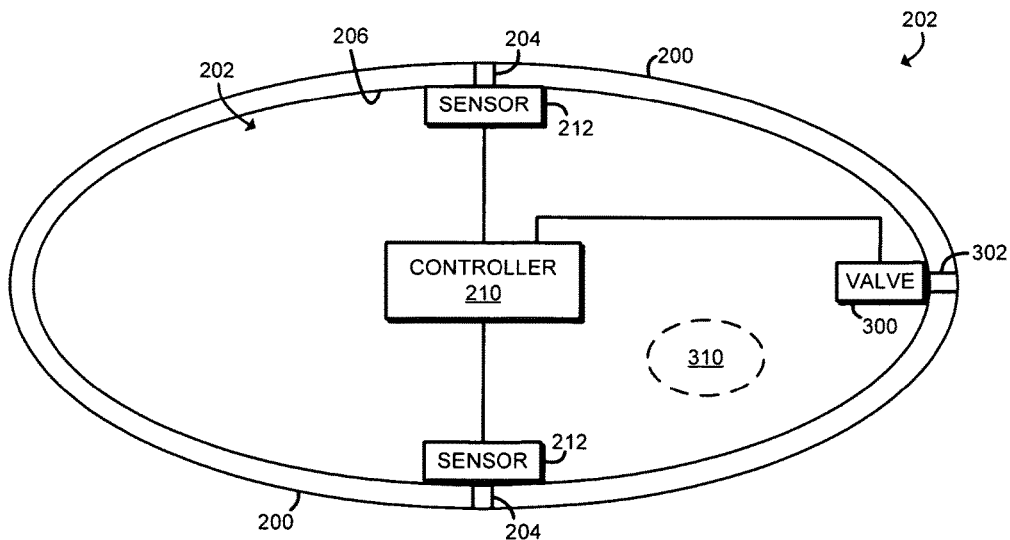
FIG. 3 is a simplified block diagram of at least one additional embodiment of a sensor mote of the system of FIG. 1.

Referring now to FIG. 3, in some embodiments, the sensor motes 102 may additionally or alternatively include a valve 300 operatively coupled to an external passageway 302. In such embodiments, the controller 210 is configured to initiate degradation of the sensor mote 102 by controlling operation of the valve 300 to allow a substance external to the sensor mote 102 to ingress into the inner chamber 202. For example, in some embodiments, the sensing location 110 may include corrosive or otherwise degradation-inducing fluids or solids that may be allowed into the inner chamber 202 via the valve 300 and passageway 302 to initiate degradation of the biodegradable portions of the controller 210 and/or housing 200. Additionally or alternatively, in some embodiments, the sensor mote 102 may include a chemical payload reservoir 310 located in the inner chamber 202. The chemical payload reservoir 310 may store a chemical capable of initiating or accelerating the biodegradation of the controller 210 and/or housing 200. Additionally, the payload reservoir 310 may be formed from a material configured to quickly degrade when exposed to the external substance (e.g., the payload reservoir 310 may be made form a water soluble material).

Figure 4:
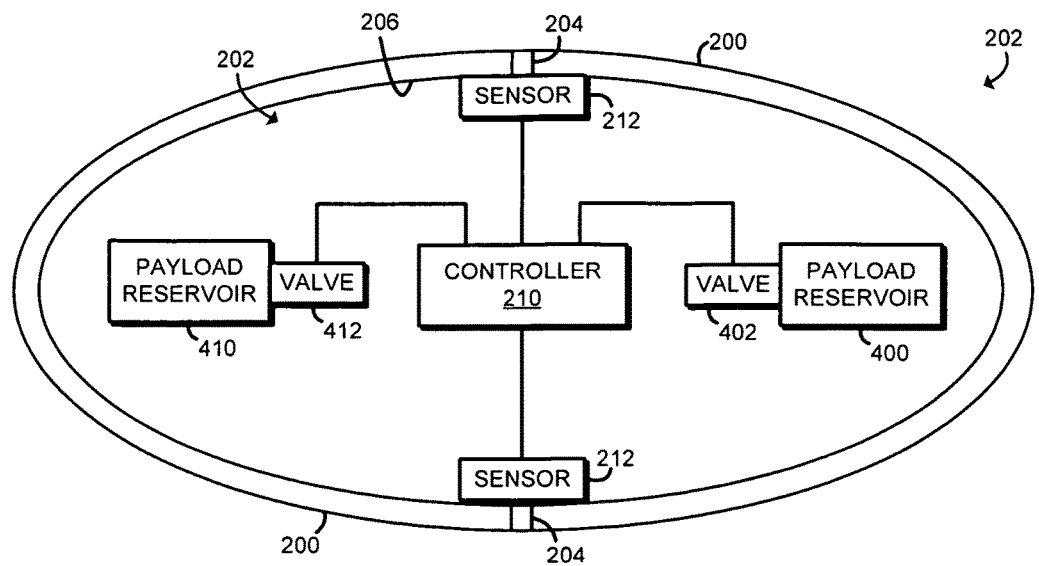
FIG. 4 is a simplified block diagram of at least one additional embodiment of a sensor mote of the system of FIG. 1.

Referring now to FIG. 4, in some embodiments, the sensor motes 102 may include multiple payload reservoirs. For example, in the illustrative embodiment, the sensor mote 102 includes a payload reservoir 400 and a payload reservoir 410. Each payload reservoir 400, 410 may store a chemical capable of degrading or accelerating the degradation of the controller 210 and/or housing 200. For example, the chemical stored by each payload reservoir 400, 410 may be the same chemical. Alternatively, in some embodiments, the chemical stored by each payload reservoir may be different. For example, in some embodiments, one payload reservoir 400, 410 may store a chemical configured to neutralize the chemical stored in the other payload reservoir 400, 410. In such embodiments, the controller 210 may be configured to control the associated valves 402, 412 of the payload reservoirs 400, 410 in a sequential manner. For example, the controller 210 may open valve 402 to release a degradation chemical from the payload reservoir 400 to initiate or accelerate the degradation of the controller 210 and/or the housing 200, and subsequently open the valve 412 of the payload reservoir 410 to release a neutralizing chemical to neutralize the degradation chemical released from the payload reservoir 400. In this way, the controller 210 may control the degradation of the sensor mote 102.

Figure 5:
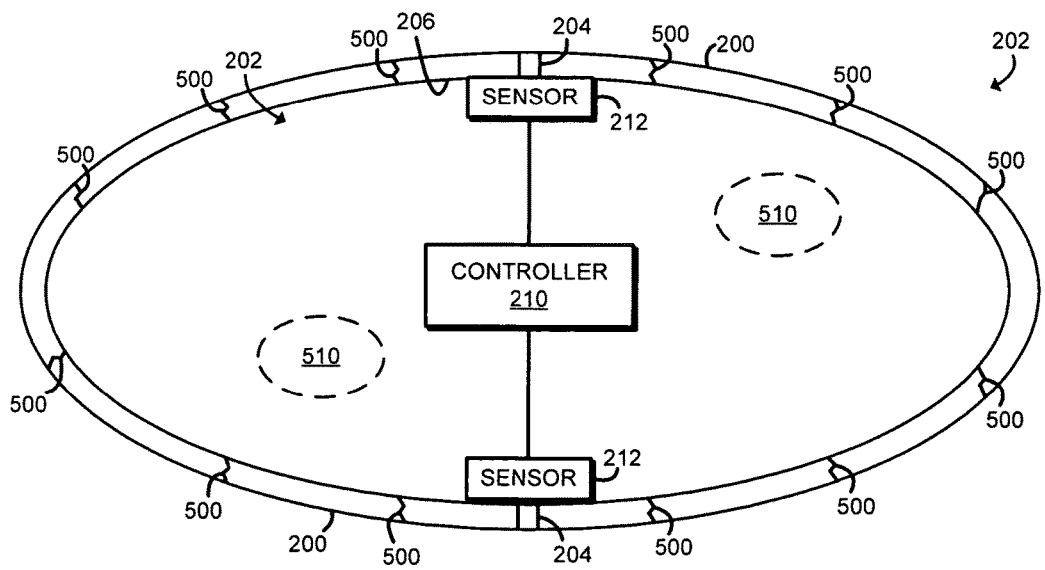
FIG. 5 is a simplified block diagram of at least one additional embodiment of a sensor mote of the system of FIG. 1.

Referring now to FIG. 5, in some embodiments, the housing 200 may include one or more predefined breakable fissures 500. The breakable fissures 500 are configured to break open in response to a trigger signal, such as a sonic wave signal, to allow a substance external to the sensor mote 102 to ingress into the inner chamber 202. In such embodiments, the sensor mote 102 may also include one or more chemical payload reservoirs 510 located in the inner chamber 202. The chemical payload reservoirs 510 may store a chemical capable of initiating or accelerating the biodegradation of the controller 210 and/or housing 200. Additionally, similar to the chemical payload reservoir 310, the payload reservoir 510 may be formed from a material configured to quickly degrade when exposed to the external substance (e.g., the payload reservoir 310 may be made form a water soluble material).

Figure 6:
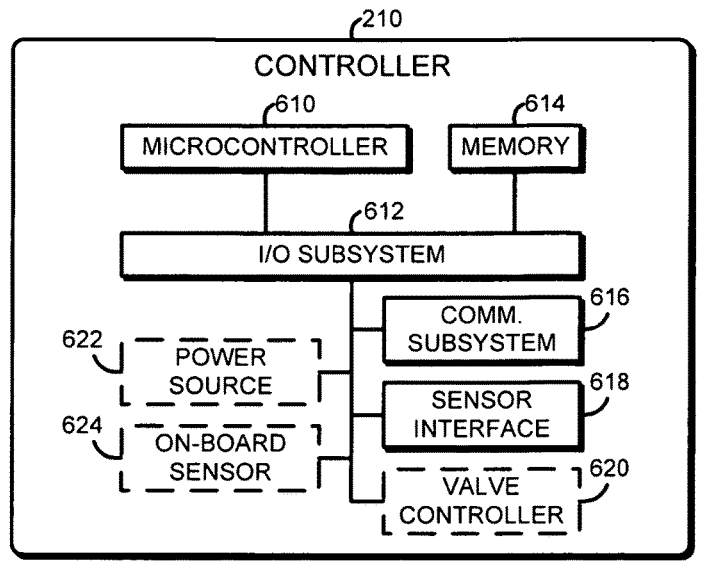
FIG. 6 is a simplified block diagram of at least one embodiment of a controller of a sensor mote of FIGS. 2-5.

Referring now to FIG. 6, the controller 210 of the sensor motes 102 may be embodied as any type of control circuit or device capable of controlling the functions of the sensor mote 102. The illustrative controller 210 includes a processor 610, an I/O subsystem 612, a memory 614, a communication subsystem 616, and a sensor interface 618. Of course, the controller 210 may include other or additional components, such as those commonly found in a control system, in other embodiments. Additionally, in some embodiments, one or more of the illustrative components may be incorporated in, or otherwise form a portion of, another component. For example, the memory 614, or portions thereof, may be incorporated in the microcontroller 610 in some embodiments.

The microcontroller 610 may be embodied as any type of microcontroller or processor capable of performing the functions described herein. For example, the microcontroller 610 may be embodied as a single or multi-core processor(s), digital signal processor, microcontroller, field programmable array (FPGA), or other processor or processing/controlling circuit. Similarly, the memory 614 may be embodied as any type of volatile or non-volatile memory or data storage capable of performing the functions described herein. In operation, the memory 614 may store various data and software used during operation of the sensor mote 102. The memory 614 is communicatively coupled to the microcontroller 610 via the I/O subsystem 612, which may be embodied as circuitry and/or components to facilitate input/output operations with the microcontroller 610, the memory 614, and other components of the sensor mote 102. For example, the I/O subsystem 612 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 612 may form a portion of a system-on-a-chip (SoC) and be incorporated, along with the microcontroller 610, the memory 614, and other components of the sensor mote 102, on a single integrated circuit chip.

The communication subsystem 616 may be embodied as any type of communication circuit, device, or collection thereof, capable of enabling communications between the sensor mote 102 and the sensor control system 104. In the illustrative embodiment, the communication subsystem 616 is embodied as an RFID communication system, which may also be used to provide power to the components of the sensor mote 102 in response to an interrogation signal as discussed below. For example, such a RFID communication system may charge a battery, capacitor, or other power source of the sensor mote 102 (e.g., the power source 622 discussed below), which may continue to power the sensor mote 102 for a period of time after receipt of the corresponding RFID scan/read.

The sensor interface 618 may be embodied as any type of input interface capable of receiving the sensor data produced by the sensors 212. In some embodiments, the sensor interface 618 may be embodied as a port of the microcontroller 610.

The controller 210 may also include a valve controller 620 in some embodiments. The valve controller 620 may be embodied as hardware circuitry configured to control the operation of the valves of payload reservoirs included in the inner chamber 202 of the sensor mote 102 and/or those valves coupled to an external passageway. As discussed above, the controller 210 is configured to control activation of such valves to initiate the degradation of the sensor motes 102.

The controller 210 may also include a power source 622 in some embodiments. In such embodiments, the power source 622 may be embodied as a battery, capacitor, supercapacitor, microsupercapacitor, or other rechargeable or non-rechargeable power source. In alternative embodiments, however, the controller 210 may be configured to receive power from an interrogation signal received via the communication subsystem 616. For example, in RFID applications, the controller 210 may be powered by the interrogation signal, which may request transmission of any collected sensor data.

As discussed above, each sensor mote may include one or more sensors 212. In addition, or alternatively, to the sensors 212, the controller 210 may include one or more on-board sensors 624. The on-board sensors 624 may be substantially similar to the sensors 212 and be configured to produce sensor data indicative of a stimulus. Unlike the sensor 212, however, the on-board sensors 624 are local to the controller 210. For example, the on-board sensors 624 may be included in a System-on-a-Chip or other integrated circuit along with other components of the controller 210.

Figure 7:
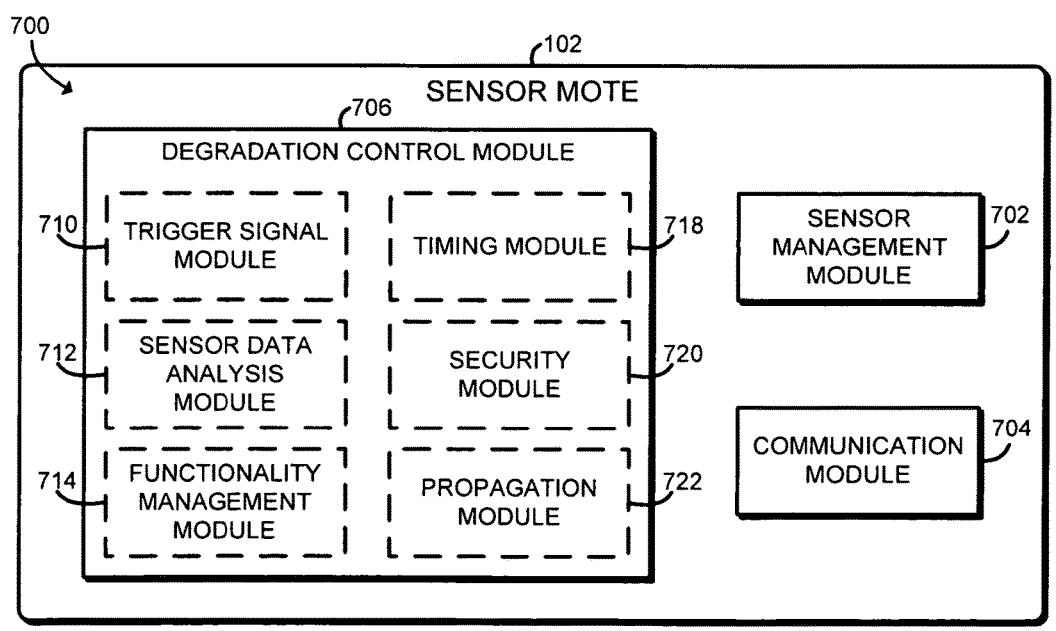
FIG. 7 is a simplified block diagram of at least one embodiment of an environment that may be established by the sensor mote of FIGS. 2-6.

Referring now to FIG. 7, in an illustrative embodiment, the sensor mote 102 establishes an environment 700 during operation. The illustrative environment 700 includes a sensor management module 702, a communication module 704, and a degradation control module 706. The various modules of the environment 700 may be embodied as hardware, firmware, software, or a combination thereof. As such, in some embodiments, one or more of the modules of the environment 700 may be embodied as circuitry or collection of electrical devices (e.g., a sensor management circuit 702, a communication circuit 704, and a degradation control circuit 706). It should be appreciated that, in such embodiments, one or more of the sensor management circuit 702, the communication circuit 704, and the degradation control circuit 706 may form a portion of one or more of the microcontroller 610, the I/O subsystem 612, and/or other components of the sensor mote 102. Additionally, in some embodiments, one or more of the illustrative modules may form a portion of another module and/or one or more of the illustrative modules may be independent of one another. Further, in some embodiments, one or more of the modules of the environment 700 may be embodied as virtualized hardware components or emulated architecture, which may be established and maintained by the microcontroller 610 or other components of the sensor mote 102.

The sensor management module 702 is configured to control operation of the sensors 212 and receive the sensor data produced by the sensors 212. In some embodiments, the sensor management module 702 may be configured to store the received sensor data for later transmission (e.g., in response to an interrogation signal). In other embodiments, the sensor management module 702 may be configured to transmit the sensor data as it's produced by the sensors 212. Additionally, depending on the functionality of the sensor mote 102, the sensor management module 702 may be configured to perform analysis on the sensor data. For example, the sensor management module 702 may be configured to monitor the sensor data and transmit a notification to the sensor control system 104 in response to the sensor data satisfying a reference threshold or other relationship.

The communication module 704 is configured to facilitate communications of the sensor mote 102 with the sensor control system 104 and/or subscription management server 120, as well as other sensor motes 102 in some embodiments. To do so, the communication module 704 may be configured to utilize any suitable communication protocol. In the illustrative embodiment, the communication module 704 is configured for RFID communications.

The degradation control module 706 is configured to monitor for a trigger event and initiate the degradation of the sensor mote 102 in response to detecting the trigger event. For example, the degradation control module 706 may include a trigger signal module 710 configured to monitor for a trigger signal received from the sensor control system 104 and/or subscription management server 120 via the communication module 704. For example, the trigger signal may be embodied as an RFID signal, which may be configured to instruct the sensor mote 102 to initiate the degradation process. In other embodiments, the trigger signal may be embodied as a wireless communication signal received from, for example, the subscription management server 120 and indicative of the expiration of a subscription service associated with the sensor motes 102. For example, the sensor motes 102 may be configured for use during a paid subscription. If the user fails to pay for the subscription service, the subscription management server 120 may transmit the trigger signal to each sensor mote 102 (e.g., via the sensor control system 104) to initiate the degradation of each sensor mote 102. In yet other embodiments, the trigger signal may be embodied as a wireless charging signal (e.g., an RFID signal). In such embodiments, the trigger signal module 710 may monitor the amount of charging supplied by the wireless charging signal and/or length or number of charge cycles and determine a trigger signal based on the charging of the sensor mote 102 (e.g., determine a trigger event after receiving a predefined number of wireless charging signals or after charging the sensor mote 102 with a predefined amount of power).

The degradation control module 706 may also include a sensor data analysis module 712 configured to analyze the sensor data produced by the sensors 212 and initiate degradation of the sensor mote 102 based on such analysis. For example, the sensor data analysis module 712 may be configured to determine whether the sensor data satisfies a reference threshold (e.g., is equal to or greater) and, if so, initiate the degradation of the sensor mote 102. In this way, the sensor mote 102 may degrade itself after a satisfactory environment of the sensing location 110 has been detected. Alternatively, in other embodiments, the sensor mote 102 may degrade itself if an unsatisfactory environment of the sensing location 110 has been detected. In such latter embodiments, the sensor mote 102 may be configured to release a chemical (e.g., via chemical payload as shown in FIGS. 3 and 5) into the sensing location 110 upon degradation to improve the environment.

In some embodiments, the sensor mote 102 may be configured to perform one or more specific functions (e.g., monitor sensor data until some condition is detected, transmit a specific amount of sensor data, etc.). In such embodiments, the degradation control module 706 may include a functionality management module 714 configured to detect completion of the prescribed functions of the sensor mote 102 and initiate degradation of the sensor mote 102 in response thereto.

The degradation control module 706 may also include a timer module 718 configured to monitor elapsed time since a temporal reference point (e.g., since implantation into the sensing location 110) and initiate degradation of the sensor mote 102 in response to a specific amount of elapsed time. For example, the sensor mote 102 may be configured to operate or otherwise be functional for only a specified period of time. In such embodiments, the timer module 718 may be reset upon receiving a corresponding reset signal. In this way, the sensor mote 102 may be configured to automatically degrade after a reference amount of time unless a reset signal has been received, which may be embodied as a subscription renewal signal received from the subscription management server 120. In some embodiments, the timer module 718 may be embodied as, or otherwise utilize, a hardware timer of the controller 210.

In some embodiments, the degradation control module 706 may also include a security module 720 configured to monitor for security events related to the sensor mote 102. For example, the security module 720 may monitor for an attempted opening of the housing 200 of the sensor mote 102 or other tampering activity. Additionally, in some embodiments, the security module 720 may monitor communications received by the sensor mote 102 for security threats. If the security module 720 detects the presence of the security threat, the security module 720 may initiate the degradation of the sensor mote 102.

Additionally, in some embodiments, the degradation control module 706 may include a propagation module 722 configured to propagate any detected trigger event to other sensor motes 102. For example, the propagation module 722 may be configured to transmit a received trigger signal to other sensor motes 102 to cause the other sensor motes 102 to initiate the degradation process. In other embodiments, the propagation of the trigger event may be performed by a release of a chemical from the sensor mote 102 that reacts with other sensor motes 102 in the sensing location 110 to initiate degradation of those other sensor motes 102.

Figure 8:
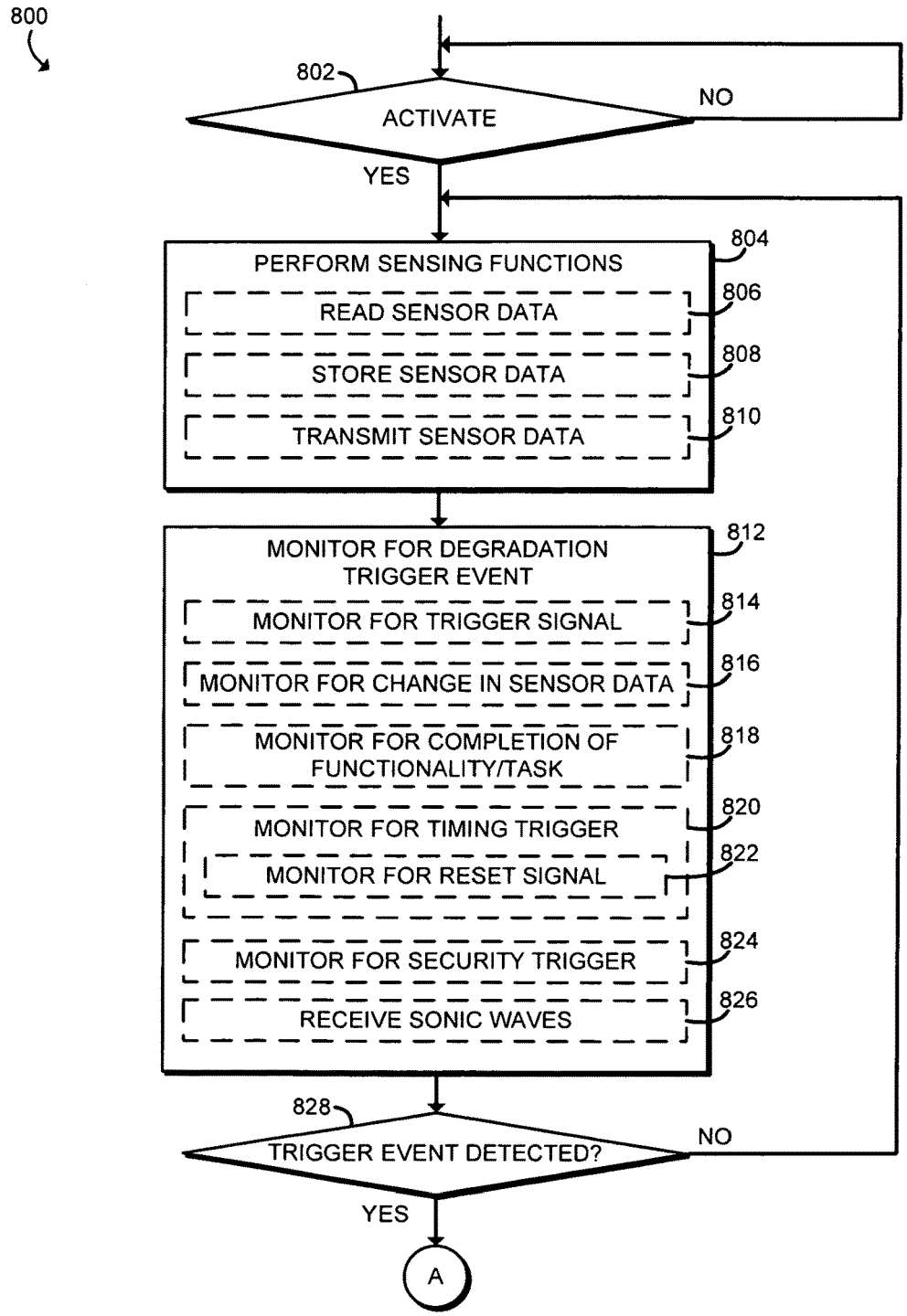
FIGS. 8 and 9 are a simplified flow diagram of at least one embodiment of a method for controlling degradation that may be executed by the sensor mote of FIGS. 2-7.
Figure 9:
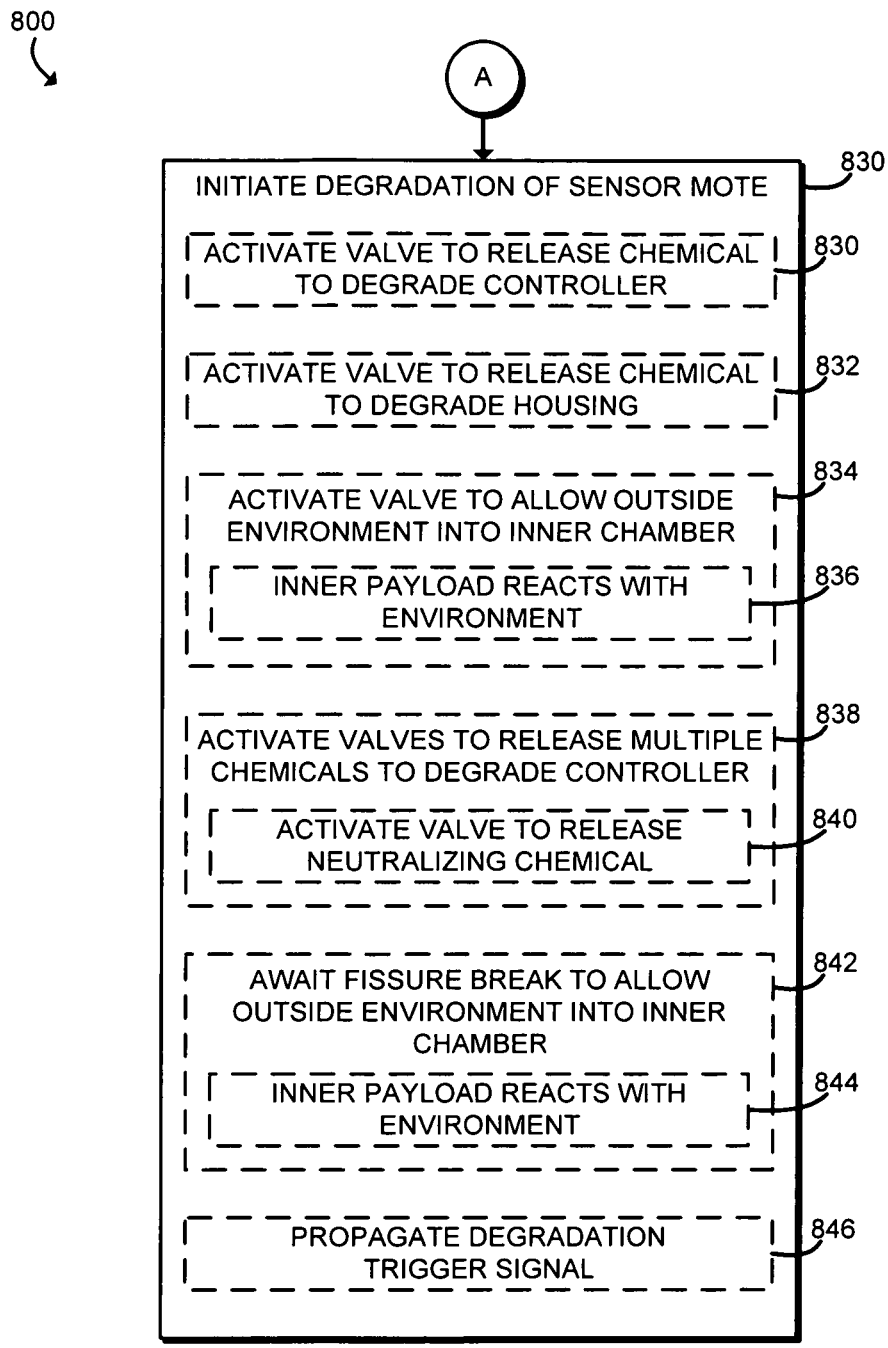

Referring now to FIGS. 8 and 9, in use, each sensor mote 102 may execute a method 800 for controlling degradation. The method 800 begins with block 802, in which the sensor mote 102 determines whether to activate. For example, in some embodiments, the sensor motes 102 may be implanted or distributed in the sensing location 110 in a dormant state. The sensor motes 102 may be configured to remain dormant until an activation signal (e.g., an RFID signal) is received. Alternatively, in other embodiments, the sensor motes 102 may be configured to begin activation after a specific period of time has elapsed. Regardless, if the sensor mote 102 determines to activate in block 802, the method 800 advances to block 804. In block 804, the sensor mote 102 performs its sensing function(s). For example, in block 806, the sensor mote 102 may read or receive sensor data from the sensors 212. Additionally, in block 808, the sensor mote 102 may store the sensor data produced by the sensors 212 (e.g., in the memory 614 of the controller 210). Further, in block 810, the sensor mote 102 may transmit the received and/or stored sensor data. For example, the sensor mote 102 may receive an interrogation signal from the sensor control system 104 and, in response, retrieve and transmit any stored sensor data to the sensor control system 104 in block 808.

After the sensor mote 102 has performed its sensing function in block 804 (or contemporaneously therewith), the sensor mote 102 monitors for a degradation trigger event in block 812. As discussed above, the trigger event may be embodied as any type of event detectable by the sensor mote 102. For example, in block 814, the sensor mote 102 may monitor for a trigger signal. As discussed above, the sensor control system 104 and/or subscription management server 120 may transmit an RFID or other wireless trigger signal to the sensor mote 102 to instruct the sensor mote 102 to initiate the degradation process. Additionally or alternatively, in block 816, the sensor mote 102 may monitor for a specific change in the sensor data and/or whether the sensor data satisfies a reference threshold. For example, sensor mote 102 may monitor for a specific condition in the environment of the sensing location 110 and initiate the degradation process in response to determining that the condition exists or has been achieved. Additionally or alternatively, in block 816, the sensor mote 102 may monitor for completion of one or more functions or tasks that the sensor mote 102 is configured to perform. Such functions or tasks may be, for example, software related, related to an effect on the environment, and/or related to some other function performed by the sensor mote 102.

The sensor mote 102 may also monitor for a timing trigger in block 820. For example, as discussed above, the sensor more 102 may be configured to monitor for an elapsed time since a temporal reference point. The sensor mote 102 may consider the elapse of the timer to be the trigger event. However, the sensor mote 102 may also monitor for a reset signal in block 822. In response to receipt of the reset signal, the sensor mote 102 may reset the timer. The sensor mote 102 may also monitor for various security events or triggers in block 824. For example, as discussed above, the sensor mote 102 may monitor for a tampering of the housing 200 and consider such tampering to be a trigger event. Further, in some embodiments in block 826, the sensor mote 102 may receive a sonic waves configured to break the predefined breakable fissures 500 (see FIG. 5). The sonic waves may be produced by, for example, the transducer 108 of the sensor control system 104.

In block 828, the sensor mote 102 determines whether a trigger event has been detected. If not, the method 800 loops back to block 804 in which the sensor mote 102 continues to perform its sensing function. If, however, the sensor mote has detected a trigger event, the method 800 advances to block 830 of FIG. 9. In block 830, the sensor mote 102 initiates the degradation process. To do so, the sensor mote 102 may perform any action capable of facilitating or accelerating the degradation of a portion of the sensor mote 102 (e.g., to accelerate the degradation of a biodegradable portion of the sensor mote 102). For example, in block 832, the sensor mote may activate a valve of a chemical payload reservoir to release a chemical stored therein to cause degradation of the controller 210. For example, in the embodiment of FIG. 2, the controller 210 may activate the valve 222 of the chemical payload reservoir 220 in block 830 to release a chemical stored therein to initiate the degradation of the controller 210 as discussed above. Additionally or alternatively, in block 832, the controller 210 may activate a valve of a chemical payload reservoir to release a chemical stored therein to cause degradation of the housing 200 of the sensor mote 102. For example, in the embodiment of FIG. 2, the controller 210 may activate the valve 232 of the chemical payload reservoir 230 in block 832 to release a chemical stored therein to initiate the degradation of the housing 200 as discussed above.

In some embodiments, the controller 210 may activate a valve to allow a substance of an outside environment to ingress into the sensor mote 102. For example, in the embodiment of FIG. 3, the controller 210 may control the valve 300 to allow a substance of the local environment to ingress into the inner chamber 202 via the external passageway 302. The foreign substance may initiate the degradation of the controller 210 and/or housing 200 as discussed above. Additionally, in some embodiments in block 840, the foreign substance may react with a chemical payload (e.g., chemical payload reservoir 310 of FIG. 3) located in the inner chamber 202 of the sensor mote 102. Such reaction may degrade the chemical payload to release a chemical stored therein, which may further the degradation of the sensor mote 102 or apply a chemical to the environment of the sensing location 110.

As discussed above in regard to FIG. 4, the sensor mote 102 may include multiple chemical payload reservoirs in some embodiments. In such embodiments, the controller 210 may control the valves of the various chemical payload reservoirs to release a chemical from each chemical payload reservoir. The release of the chemical may initiate the degradation of the sensor mote 102 as discussed above. In some embodiments, one or more of the released chemicals may be configured to neutralize another released chemical in block 840. In that way, the controller 210 may control the degradation of the sensor mote 102 by initiating and stopping the degradation process based on the release of the neutralizing chemical.

Additionally, as discussed above in regard to FIG. 5, the housing 200 of the sensor mote 102 may include one or more predefined breakable fissures. In such embodiments, the controller 210 may be configured to await the breakage of one or more of the breakable fissures in block 844. For example, the sensor control system 104 may apply, via the transducer 108, a sonic wave to the sensing location 110 to cause the breakable fissures of the sensor motes to open. If so, a substance from the external environment may ingress into the inner chamber 202 of the sensor mote 102 and react with a chemical payload (e.g., chemical payload reservoir 510 of FIG. 5) located in the inner chamber 202 of the sensor mote 102. Such reaction may degrade the chemical payload to release a chemical stored therein, which may further the degradation of the sensor mote 102 or apply a chemical to the environment of the sensing location 110.

In addition to the self-degradation process, one or more of the sensor motes 102 may be configured to propagate the trigger event to other sensor motes 102 in block 846. To do so, for example, a sensor mote 102 may wireless transmit a trigger signal to other sensor motes 102 to cause the other sensor motes to initiate the degradation process. Additionally or alternatively, the trigger event may be propagated to other sensor motes 102 via the release of a chemical into the sensing location 110, which may initiate the degradation of the other sensor motes 102.

After the sensor mote 102 has initiated the degradation process, the sensor mote 102 may halt all functions. However, because the sensor mote 102 is self-degrading, the sensor mote 102 need not be recovered after use unlike typical sensor devices.

Examples

Illustrative examples of the technologies disclosed herein are provided below. An embodiment of the technologies may include any one or more, and any combination of, the examples described below.

Example 1 includes a sensor mote for performing a sensor function. The sensor mote includes at least one sensor to produce sensor data indicative of a sensed stimulus; a controller to receive the sensor data and control operations of the sensor mote, wherein at least a portion of the sensor mote is biodegradable and the controller is to detect a trigger event and initiate degradation of the portion of the sensor mote in response to detection of the trigger event.

Example 2 includes the subject matter of Example 1, and wherein the trigger event comprises a trigger signal, and further comprising a communication subsystem to receive the trigger signal.

Example 3 includes the subject matter of any of Examples 1 or 2, and wherein the trigger signal comprises a radio-frequency identification signal.

Example 4 includes the subject matter of any of Examples 1-3, and wherein the trigger signal comprises a wireless communication signal transmitted by a remote subscription server and indicative of a lapsed subscription service.

Example 5 includes the subject matter of any of Examples 1-4, and wherein the controller is further to compare the sensor data to a reference threshold and detect the trigger event in response to a determination that the sensor data satisfies the reference threshold.

Example 6 includes the subject matter of any of Examples 1-5, and wherein the control is to perform a function based on the sensor data and detect the trigger event in response to a determination that the function has been completed.

Example 7 includes the subject matter of any of Examples 1-6, and further comprising a timer and wherein the controller is to detect the trigger event in response to an expiration of the timer.

Example 8 includes the subject matter of any of Examples 1-7, and further comprising a communication subsystem to receive a reset signal, and wherein the controller is further to reset the timer in response to receipt of the reset signal prior to expiration of the timer.

Example 9 includes the subject matter of any of Examples 1-8, and wherein the controller is further to detect a security event associated with the sensor mote.

Example 10 includes the subject matter of any of Examples 1-9, and further comprising a housing, wherein the controller is located in the housing and the security event is indicative of an attempted opening of the housing.

Example 11 includes the subject matter of any of Examples 1-10, and wherein to detect the trigger event comprises to detect a sonic wave applied to an environment of the sensor mote.

Example 12 includes the subject matter of any of Examples 1-11, and wherein at least a portion of the controller is degradable and the controller is initiate degradation of the controller in response to the detection of the trigger event.

Example 13 includes the subject matter of any of Examples 1-12, and further comprising a housing, wherein the controller is located in the housing and at least a portion of the housing is biodegradable, and wherein the controller is to initiate degradation of the housing in response to the detection of the trigger event.

Example 14 includes the subject matter of any of Examples 1-13, and further a housing and a chemical reservoir, wherein the controller and the chemical reservoir are located in the housing, and wherein the controller is to control a valve of the chemical reservoir to release a chemical stored therein to cause the degradation of the portion of the sensor mote.

Example 15 includes the subject matter of any of Examples 1-14, and wherein the portion of the sensor mote comprises a portion of the controller.

Example 16 includes the subject matter of any of Examples 1-15, and further comprising a housing, wherein the controller is located in the housing and the portion of the sensor mote comprises a portion of the housing.

Example 17 includes the subject matter of any of Examples 1-16, and further comprising a housing and a valve coupled to the housing, wherein the controller is located in the housing, and wherein the controller is to control the valve to allow a substance from an environment external to the sensor mote into the housing of the sensor mote cause degradation of the portion of the sensor mote.

Example 18 includes the subject matter of any of Examples 1-17, and further comprising a chemical payload located in the housing and wherein to control the valve comprises to open the valve to allow the substance from the environment external to the sensor mote into the housing of the sensor mote to react with the chemical.

Example 19 includes the subject matter of any of Examples 1-18, and further a housing, a first chemical reservoir, and a second chemical reservoir, wherein the controller, the first chemical reservoir, and the second chemical reservoir are located in the housing, and wherein the controller is further to (i) control a first valve of the first chemical reservoir to release a first chemical from the first chemical reservoir to cause the degradation of the portion of the sensor mote and (ii) control a second valve of the second chemical reservoir to release a second chemical from the second chemical reservoir.

Example 20 includes the subject matter of any of Examples 1-19, and wherein the second chemical is configured to neutralize the first chemical when released.

Example 21 includes the subject matter of any of Examples 1-20, and further comprising a housing, wherein the controller is located in the housing and the housing comprises a plurality of predefined breakable fissures in the housing, wherein the housing is configured to allow the predefined breakable fissures to open to expose a chemical payload included inside the housing to a substance from an environment external to the sensor mote.

Example 22 includes the subject matter of any of Examples 1-21, and further comprising a communication subsystem to transmit a trigger signal to the another sensor mote in response to detection of the trigger event.

Example 23 includes a method for controlling degradation of a sensor mote. The method includes producing, by a sensor of the sensor mote, sensor data indicative of a sensed stimulus; detecting, by a controller of the sensor mote, a trigger event; and initiating, by the controller, degradation of at least a portion of the sensor mote in response to detection of the trigger event.

Example 24 includes the subject matter of Example 23, and wherein detecting the trigger event comprises receiving, by a communication subsystem of the controller, a trigger signal.

Example 25 includes the subject matter of any of Examples 23 and 24, and wherein receiving the trigger signal comprises receiving a radio-frequency identification signal.

Example 26 includes the subject matter of any of Examples 23-25, and wherein receiving the trigger signal comprises receiving a wireless communication signal from a remote subscription server, wherein the wireless communication signal is indicative of a lapsed subscription service.

Example 27 includes the subject matter of any of Examples 23-26, and further comprising comparing, by the controller, the sensor data to a reference threshold, and wherein detecting the trigger event comprises determining, by the controller, that the sensor data satisfies the reference threshold.

Example 28 includes the subject matter of any of Examples 23-27, and further comprising performing, by the controller, a function based on the sensor data, and wherein detecting the trigger event comprises detecting, by the controller, completion of the function.

Example 29 includes the subject matter of any of Examples 23-28, and wherein detecting the trigger event comprises detecting, by the controller, expiration of a timer of the sensor mote.

Example 30 includes the subject matter of any of Examples 23-29, and further comprising receiving, by a communication subsystem of the controller, a reset signal; and resetting, by the controller, the timer in response to the reset signal and prior to expiration of the timer.

Example 31 includes the subject matter of any of Examples 23-30, and wherein detecting the trigger event comprises detecting a security event associated with the sensor mote.

Example 32 includes the subject matter of any of Examples 23-31, and wherein detecting the security event comprise detecting, by the controller, an attempted opening of a housing of the sensor mote.

Example 33 includes the subject matter of any of Examples 23-32, and wherein detecting the trigger event comprises detecting a sonic wave applied to an environment of the sensor mote.

Example 34 includes the subject matter of any of Examples 23-33, and wherein initiating degradation of at least a portion of the sensor mote comprises initiating, by the controller, degradation of at least a portion of the controller in response to the detection of the trigger event.

Example 35 includes the subject matter of any of Examples 23-34, and wherein initiating degradation of at least a portion of the sensor mote comprises initiating, by the controller, degradation of a housing of the sensor mote in response to the detection of the trigger event.

Example 36 includes the subject matter of any of Examples 23-35, and wherein initiating degradation of at least a portion of the sensor mote comprises controlling, by the controller, a valve of a chemical reservoir included in the sensor mote to release a chemical from the chemical reservoir to cause the degradation of the portion of the sensor mote.

Example 37 includes the subject matter of any of Examples 23-36, and wherein controlling the valve of the chemical reservoir comprises controlling the valve of the chemical reservoir to release the chemical from the chemical reservoir to cause the degradation of the controller.

Example 38 includes the subject matter of any of Examples 23-37, and wherein controlling the valve of the chemical reservoir comprises controlling the valve of the chemical reservoir to release the chemical from the chemical reservoir to cause the degradation of a housing of the sensor mote.

Example 39 includes the subject matter of any of Examples 23-38, and wherein initiating degradation of at least a portion of the sensor mote comprises controlling, by the controller, a valve connected to a housing of the sensor mote to allow a substance from an environment external to the sensor mote into the housing of the sensor mote to cause the degradation of the portion of the sensor mote.

Example 40 includes the subject matter of any of Examples 23-39, and wherein controlling the valve connected to the housing comprises opening the valve to allow the substance from the environment external to the sensor mote into the housing of the sensor mote to react with a chemical payload included inside the housing of the sensor mote.

Example 41 includes the subject matter of any of Examples 23-40, and wherein initiating degradation of at least a portion of the sensor mote comprises controlling, by the controller, a first valve of a first chemical reservoir included in the sensor mote to release a first chemical from the first chemical reservoir to cause the degradation of the portion of the sensor mote; and controlling, by the controller, a second valve of a second chemical reservoir included in the sensor mote to release a second chemical from the second chemical reservoir.

Example 42 includes the subject matter of any of Examples 23-41, and wherein controlling the second valve of the second chemical reservoir comprises releasing the second chemical from the second chemical reservoir to neutralize the first chemical.

Example 43 includes the subject matter of any of Examples 23-42, and wherein initiating degradation of at least a portion of the sensor mote comprises exposing a chemical payload included inside the housing to a substance from an environment external to the sensor mote via a predefined breakable fissure in a housing of the sensor mote.

Example 44 includes the subject matter of any of Examples 23-43, and further comprising communicating the trigger event to another sensor mote to cause degradation of at least a portion of the another sensor mote.

Example 45 includes the subject matter of any of Examples 23-44, and wherein communicating the trigger event comprises transmitting, by a communication subsystem of the controller, a trigger signal to the another sensor mote in response to detecting the trigger event.

Example 46 includes the subject matter of any of Examples 23-45, and wherein communicating the trigger event comprises communicating the trigger event via a release of a chemical by the sensor mote in response to detecting the trigger event.

Example 47 includes one or more computer-readable storage media comprising a plurality of instructions that, when executed, cause a sensor mote to perform the method of any of Examples 23-46.

Example 48 includes a sensor mote for performing a sensor function. The sensor mote includes means for producing sensor data indicative of a sensed stimulus; means for detecting a trigger event; and means for initiating degradation of at least a portion of the sensor mote in response to detection of the trigger event.

Example 49 includes the subject matter of Example 48, and wherein the means for detecting the trigger event comprises means for receiving a trigger signal.

Example 50 includes the subject matter of any of Examples 48 or 49, and wherein the means for receiving the trigger signal comprises means for receiving a radio-frequency identification signal.

Example 51 includes the subject matter of any of Examples 48-50, and wherein the means for receiving the trigger signal comprises means for receiving a wireless communication signal from a remote subscription server, wherein the wireless communication signal is indicative of a lapsed subscription service.

Example 52 includes the subject matter of any of Examples 48-51, and further comprising means for comparing the sensor data to a reference threshold, and wherein the means for detecting the trigger event comprises means for determining that the sensor data satisfies the reference threshold.

Example 53 includes the subject matter of any of Examples 48-52, and further comprising means for performing a function based on the sensor data, and wherein the means for detecting the trigger event comprises detecting completion of the function.

Example 54 includes the subject matter of any of Examples 48-53, and wherein the means for detecting the trigger event comprises means for detecting expiration of a timer of the sensor mote.

Example 55 includes the subject matter of any of Examples 48-54, and further comprising means for receiving a reset signal; and means for resetting the timer in response to the reset signal and prior to expiration of the timer.

Example 56 includes the subject matter of any of Examples 48-55, and wherein the means for detecting the trigger event comprises means for detecting a security event associated with the sensor mote.

Example 57 includes the subject matter of any of Examples 48-56, and wherein the means for detecting the security event comprise means for detecting an attempted opening of a housing of the sensor mote.

Example 58 includes the subject matter of any of Examples 48-57, and wherein the means for detecting the trigger event comprises means for detecting a sonic wave applied to an environment of the sensor mote.

Example 59 includes the subject matter of any of Examples 48-58, and wherein the means for initiating degradation of at least a portion of the sensor mote comprises means for initiating degradation of at least a portion of the controller in response to the detection of the trigger event.

Example 60 includes the subject matter of any of Examples 48-59, and wherein the means for initiating degradation of at least a portion of the sensor mote comprises means for initiating degradation of a housing of the sensor mote in response to the detection of the trigger event.

Example 61 includes the subject matter of any of Examples 48-60, and wherein the means for initiating degradation of at least a portion of the sensor mote comprises means for controlling a valve of a chemical reservoir included in the sensor mote to release a chemical from the chemical reservoir to cause the degradation of the portion of the sensor mote.

Example 62 includes the subject matter of any of Examples 48-61, and wherein the means for controlling the valve of the chemical reservoir comprises means for controlling the valve of the chemical reservoir to release the chemical from the chemical reservoir to cause the degradation of the controller.

Example 63 includes the subject matter of any of Examples 48-62, and wherein the means for controlling the valve of the chemical reservoir comprises means for controlling the valve of the chemical reservoir to release the chemical from the chemical reservoir to cause the degradation of a housing of the sensor mote.

Example 64 includes the subject matter of any of Examples 48-63, and wherein the means for initiating degradation of at least a portion of the sensor mote comprises means for controlling a valve connected to a housing of the sensor mote to allow a substance from an environment external to the sensor mote into the housing of the sensor mote to cause the degradation of the portion of the sensor mote.

Example 65 includes the subject matter of any of Examples 48-64, and wherein the means for controlling the valve connected to the housing comprises means for opening the valve to allow the substance from the environment external to the sensor mote into the housing of the sensor mote to react with a chemical payload included inside the housing of the sensor mote.

Example 66 includes the subject matter of any of Examples 48-65, and wherein the means for initiating degradation of at least a portion of the sensor mote comprises means for controlling a first valve of a first chemical reservoir included in the sensor mote to release a first chemical from the first chemical reservoir to cause the degradation of the portion of the sensor mote; and means for controlling a second valve of a second chemical reservoir included in the sensor mote to release a second chemical from the second chemical reservoir.

Example 67 includes the subject matter of any of Examples 48-66, and wherein means for controlling the second valve of the second chemical reservoir comprises means for releasing the second chemical from the second chemical reservoir to neutralize the first chemical.

Example 68 includes the subject matter of any of Examples 48-67, and wherein the means for initiating degradation of at least a portion of the sensor mote comprises means for exposing a chemical payload included inside the housing to a substance from an environment external to the sensor mote via a predefined breakable fissure in a housing of the sensor mote.

Example 69 includes the subject matter of any of Examples 48-68, and further comprising means for communicating the trigger event to another sensor mote to cause degradation of at least a portion of the another sensor mote.

Example 70 includes the subject matter of any of Examples 48-69, and wherein the means for communicating the trigger event comprises means for transmitting a trigger signal to the another sensor mote in response to detecting the trigger event.

Example 71 includes the subject matter of any of Examples 48-70, and wherein the means for communicating the trigger event comprises means for communicating the trigger event via a release of a chemical by the sensor mote in response to detecting the trigger event.

The invention claimed is:

1. A sensor mote for performing a sensor function, the sensor mote comprising:
   a housing, wherein at least a portion of the housing is biodegradable;
   at least one sensor located in the housing to produce sensor data indicative of a sensed stimulus;

a controller located in the housing to receive the sensor data and control operations of the sensor mote, wherein the controller is to detect a trigger event and initiate degradation of the portion of the housing in response to detection of the trigger event; and a communication subsystem to transmit a trigger signal to an another sensor mote in response to detection of the trigger event.

2. The sensor mote of claim 1, further comprising a chemical reservoir, wherein the chemical reservoir is located in the housing, and wherein the controller is to control a valve of the chemical reservoir to release a chemical stored therein to cause the degradation of the portion of the housing.

3. The sensor mote of claim 1, further comprising a valve coupled to the housing, and wherein the controller is to control the valve to allow a substance from an environment external to the sensor mote into the housing of the sensor mote to cause degradation of the portion of the housing.

4. The sensor mote of claim 3, further comprising a chemical payload located in the housing and wherein to control the valve comprises to open the valve to allow the substance from the environment external to the sensor mote into the housing of the sensor mote to react with the chemical payload.

5. The sensor mote of claim 1, further comprising a first chemical reservoir and a second chemical reservoir, wherein the first chemical reservoir and the second chemical reservoir are located in the housing, and wherein the controller is further to (i) control a first valve of the first chemical reservoir to release a first chemical from the first chemical reservoir to cause the degradation of the portion of the housing and (ii) control a second valve of the second chemical reservoir to release a second chemical from the second chemical reservoir.

6. The sensor mote of claim 1, wherein the housing comprises a plurality of predefined breakable fissures in the housing, wherein the housing is configured to allow the predefined breakable fissures to open to expose a chemical payload included inside the housing to a substance from an environment external to the sensor mote.

7. A method for controlling degradation of a sensor mote, the method comprising:

producing, by a sensor located in a housing of the sensor mote, sensor data indicative of a sensed stimulus, wherein at least a portion of the housing is biodegradable;

detecting, by a controller located in the housing of the sensor mote, a trigger event;

transmitting, by a communication subsystem located in the housing of the sensor mote, a trigger signal to an another sensor mote in response to detection of the trigger event; and initiating, by the controller, degradation of at least a portion of the housing in response to detection of the trigger event.

8. The method of claim 7, wherein initiating degradation of at least a portion of the housing comprises controlling, by the controller, a valve of a chemical reservoir included in the sensor mote to release a chemical from the chemical reservoir to cause the degradation of the portion of the housing.

9. The method of claim 7, wherein initiating degradation of at least a portion of the housing comprises controlling, by the controller, a valve connected to a housing of the sensor mote to allow a substance from an environment external to the sensor mote into the housing of the sensor mote to cause the degradation of the portion of the housing.

10. The method of claim 9, wherein controlling the valve connected to the housing comprises opening the valve to allow the substance from the environment external to the sensor mote into the housing of the sensor mote to react with a chemical payload included inside the housing of the sensor mote.

11. The method of claim 7, wherein initiating degradation of at least a portion of the housing comprises:

controlling, by the controller, a first valve of a first chemical reservoir included in the sensor mote to release a first chemical from the first chemical reservoir to cause the degradation of the portion of the housing; and controlling, by the controller, a second valve of a second chemical reservoir included in the sensor mote to release a second chemical from the second chemical reservoir.

12. The method of claim 7, wherein initiating degradation of at least a portion of the housing comprises exposing a chemical payload included inside the housing to a substance from an environment external to the sensor mote via a predefined breakable fissure in a housing of the sensor mote.

13. The method of claim 7, further comprising communicating the trigger event to another sensor mote to cause degradation of at least a portion of the another sensor mote's housing.

14. The method of claim 13, wherein communicating the trigger event comprises communicating the trigger event via a release of a chemical by the sensor mote in response to detecting the trigger event.

15. One or more non-transitory, computer-readable storage media comprising a plurality of instructions that, when executed, cause a sensor mote to:

obtain, from a sensor located in a housing of the sensor mote, sensor data indicative of a sensed stimulus, wherein at least a portion of the housing is biodegradable;

detect a trigger event transmit a trigger signal to an another sensor mote in response to detection of the trigger event; and initiate degradation of at least a portion of housing in response to detection of the trigger event.

16. The one or more non-transitory, computer-readable storage media of claim 15, wherein to detect the trigger event comprises to receive a trigger signal.

17. The one or more non-transitory computer-readable storage media of claim 15, wherein to initiate degradation of at least a portion of the housing comprises to control a valve of a chemical reservoir included in the sensor mote to release a chemical from the chemical reservoir to cause the degradation of the portion of the housing.

18. The one or more non-transitory, computer-readable storage media of claim 15, wherein to initiate degradation of at least a portion of the housing comprises to control a valve connected to a housing of the sensor mote to allow a substance from an environment external to the sensor mote into the housing of the sensor mote to cause the degradation of the portion of the housing.

19. The one or more non-transitory, computer-readable storage media of claim 18, wherein to control the valve connected to the housing comprises to open the valve to allow the substance from the environment external to the sensor mote into the housing of the sensor mote to react with a chemical payload included inside the housing of the sensor mote.

20. The one or more non-transitory, computer-readable storage media of claim 15, wherein to initiate degradation of at least a portion of the housing comprises to:
   control a first valve of a first chemical reservoir included in the sensor mote to release a first chemical from the first chemical reservoir to cause the degradation of the portion of the housing; and
   control a second valve of a second chemical reservoir included in the sensor mote to release a second chemical from the second chemical reservoir.

21. The one or more non-transitory, computer-readable storage media of claim 15, wherein to initiate degradation of at least a portion of the housing comprises to expose a chemical payload included inside the housing to a substance from an environment external to the sensor mote via a predefined breakable fissure in a housing of the sensor mote.

22. The one or more non-transitory, computer-readable storage media of claim 15, wherein the plurality of instructions, when executed, cause a sensor mote to communicate the trigger event to another sensor mote to cause degradation of at least a portion of the another sensor mote's housing.

* * * * *